(12) United States Patent
Veer et al.

(10) Patent No.: US 6,248,548 B1
(45) Date of Patent: Jun. 19, 2001

(54) THROMBOSIS PROPHYLAXIS FOR FACTOR V$^{LEIDEN}$ CARRIERS

(75) Inventors: Cornelis Van't Veer; Michael Kalafatis, both of Burlington; Kenneth G. Mann, Shelburne, all of VT (US)

(73) Assignee: The University of Vermont and State Agriculture College

( * ) Notice: Subject to any disclaimer, the term of this patent is extended or adjusted under 35 U.S.C. 154(b) by 0 days.

(21) Appl. No.: 09/431,103

(22) Filed: Nov. 1, 1999

Related U.S. Application Data

(62) Division of application No. 08/707,782, filed on May 8, 1996, now Pat. No. 5,977,057.

(51) Int. Cl.$^7$ ................ C12Q 1/56; C12Q 1/68; C07K 14/00; C07K 1/00; A01N 37/18
(52) U.S. Cl. ............... 435/13; 435/6; 530/300; 530/350; 514/2; 514/8
(58) Field of Search .............. 435/13, 69.6, 6; 530/300, 350; 514/2, 8

(56) References Cited

U.S. PATENT DOCUMENTS 5,874,256 * 2/1999 Bertina et al. .............. 435/69.6

FOREIGN PATENT DOCUMENTS

WO 91/02753  8/1990  (WO) .

OTHER PUBLICATIONS

Kalafatis et al., "Characterization of the Molecular Defect in Factor V$^{R506Q}$", *J. Biol. Chem.*, 270(8):4053–4057 (1995).
Novotny et al., "Plasma Antigen Levels of the Lipoprotein–Associated Coagulation Inhibitor in Patient Samples", *Blood*κ(2):387–393 (1991).
Bertina et al. Nature (1994)369: 64–67.
Hamamoto et al. J. Biol. Chem. (1993)268 (12): 8704–8710.
van's Veer, C., and Mann, K.G., (1995) Blood 86 suppl. 1, 448a, abstract 1777.
van't Veer, C., Kalafatis, M., and Mann, K.G. (1995) Blood 86 suppl. 1, 285a abstract 1128.
van't Veer, C. et al., The Journal of Biological Chemistry Increased Tissue Factor–initiated Prothrombin Activation as a Result of the Arg506—Gin Mutation in Factor V$^{leiden}$ vol. 272, No. 33, Aug. 15, 1997 pp. 20721–20729.
van't Veer, C., et al., The Journal of Biological Chemistry "Inhibitory Mechanism of the Protein C. Pathway on Tissue Factor–induced Thrombin Generation" vol. 272, No. 12, Mar. 21, 1997, pp. 7983–7994.

* cited by examiner

Primary Examiner—Ponnathapu Achutmurthy
Assistant Examiner—Tekchand Saidha
(74) Attorney, Agent, or Firm—Banner& Witcoff, Ltd.

(57) ABSTRACT

Persons having the Factor V$^{LEIDEN}$ mutation and a lower than average plasma level of TFPI have been found to be at elevated risk of thrombosis. Prophylactic methods for reducing the risk of thrombosis employ the administration of TFPI to achieve higher levels in the plasma.

3 Claims, 6 Drawing Sheets

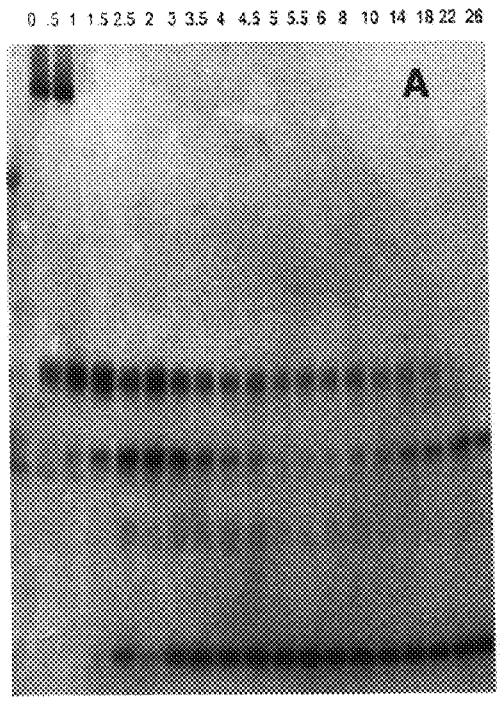
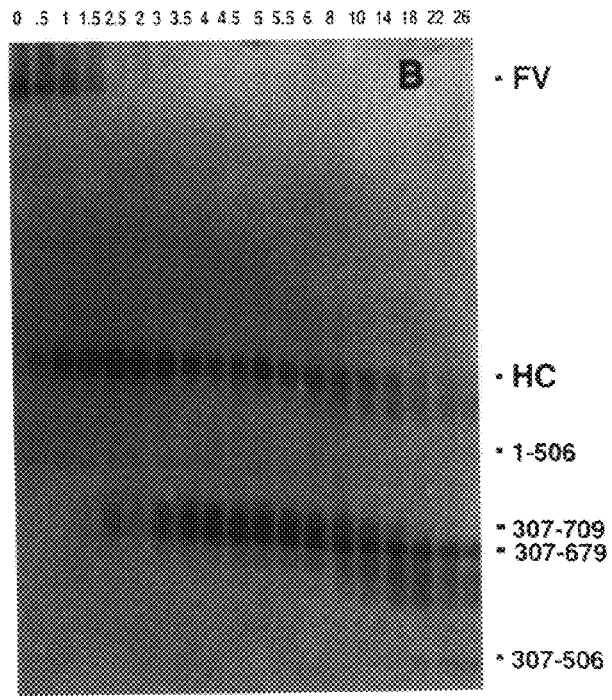
FIG. 2A
FIG. 2B

THROMBOSIS PROPHYLAXIS FOR FACTOR V$^{LEIDEN}$ CARRIERS

This application is a divisional application of Ser. No. 08/707,782, filed May 8, 1996 now U.S. Pat. No. 5,977,057.

BACKGROUND OF THE INVENTION

The extrinsic pathway of blood coagulation involves the sequential activation of coagulation factors initiated by tissue factor (TF) leading to thrombin generation. The thrombin initially produced causes platelets to aggregate and generates a fibrin network. The fibrin network stabilizes the platelet aggregate forming the hemostatic plug which maintains the integrity of the circulatory system after vessel wall damage. The deregulation of the anticoagulant pathways, which effectively restrict hemostatic reactions to local vascular damage with responses of appropriate intensity may lead to the unwanted occlusion of blood vessels, i.e., thrombosis.

The procoagulant process which leads to thrombin formation starts with the binding of factor VII(a) to its cofactor tissue factor (TF), an integral membrane protein which is exposed by cellular injury. The factor VIIa·TF complex converts the zymogens actor X and factor IX into active enzymes by limited proteolysis (1). Activated factor IX (factor IXa) binds to its cofactor, factor VIIIa, after its activation, to form a second complex which activates factor X at a more efficient rate than factor VIIa·TF. Activated factor X (factor Xa) in complex with activated factor V (factor Va) forms the prothrombinase complex (factor Xa·factor Va), which converts prothrombin into thrombin. A phospholipid membrane provided by damaged and/or activated cells is essential for the assembly of each of the vitamin K dependent enzyme complexes. [For reviews on blood coagulation and the phospholipid dependent reactions is blood coagulation see respectively references 2 and 3.] Once formed, thrombin accelerates its own generation by positive feedback reactions. Thrombin activates the procofactors factor V and factor VIII by limited proteolysis into their active forms and may also activate factor XI which can accelerate the reaction by factor IX activation (4).

In normal hemostasis the procoagulant system is retarded by anticoagulant mechanisms which serve to localize and attenuate the hemostatic reaction. The anticoagulant systems consist of stoichiometric protease inhibitors and the dynamic protein C pathway. The tissue factor pathway inhibitor (TFPI) is a stoichiometric protease inhibitor which regulates the initiation of coagulation by inhibition of factor VIIa·TF activity in a factor Xa dependent manner. [For a review on TFPI see reference 5.] TFPI inhibits the proteolytic activity of factor Xa by reversible binding to the active site of factor Xa. Factor Xa is a cofactor for TFPI inhibition of factor VIIa·TF activity by formation of a quaternary complex factor Xa·TFPI·factor VIIa·TF. Although no deficiency states are known in humans, in vivo the relevance of TFPI was shown in rabbits by the sensitization to TF triggered disseminated intravascular coagulation (DIC) after immunodepletion of TFPI (6). The inhibition was suggested to be primarily the result of inhibition of factor VIIa·TF since DIC triggered by factor Xa directly was not affected by TFPI (7). At plasma concentrations of TFPI, direct inhibition of prothrombinase activity is only moderate (8) while inhibition of factor VIIa·TF activity goes to completion in the presence of physiological concentrations of TFPI (9,10) when factor Xa is present.

A dynamic negative feedback mechanism for thrombin activation is provided by the protein C pathway. This pathway is initiated with the binding of thrombin to thrombomodulin, which is constitutively expressed by endothelial cells. [For a review on thrombomodulin and protein C see reference 12]. The thrombin·thrombomodulin complex activates plasma protein C. Thrombin alone may activate protein C in the absence of calcium ions, however at physiologic concentrations of calcium ions thrombomodulin is required to activate protein C at a significant rate. Recently the first report of an individual suffering from thrombosis associated with a thrombomodulin mutation leading to a defective protein was published (13). The thrombotic events observed in the reported thrombomodulin deficient individual conclusively identifies the significance of thrombomodulin as a natural anticoagulant.

The important role of protein C as an anticoagulant was secured by numerous reports of thrombotic complications in protein C deficient individuals. Activated protein C exerts its inhibitory effect on coagulation by proteolytic inactivation of the procofactors factor V and factor VIII and/or their activated forms, factor Va and factor VIIIa (15–23).

The inactivation of human factor Va occurs largely as a sequential process (26,27). The preferred first cleavage occurs at Arg$^{506}$ and is followed by cleavage at Arg$^{306}$ and Arg$^{679}$. The phospholipid dependent cleavage at Arg$^{306}$ is associated with the major loss of cofactor activity (26,27), while cleavage at Arg$^{506}$ is only accompanied by a limited loss of activity. A poor anticoagulant response of plasma to activated protein C (24) was recently correlated with a single point mutation in the factor V$^{LEIDEN}$ gene which leads to an Arg$^{506}$→Gln substitution in the factor V molecule (25). Approximately 3–5% of the Caucasian population is heterozygous for this mutation which is associated with ~20% of the cases of familial thrombosis (25). The observed APC resistance of factor VArg$^{506}$→Gln is caused by a slower inactivation by APC of activated factor V$^{LEIDEN}$ because it lacks the APC cleavage site at Arg$^{506}$ (26). The observed "resistances" toward APC inactivation of factor VArg$^{506}$→Gln is a consequence of slower cleavage at Arg306 when the 506–507 peptide bond is intact(26). Inactivation of the procofactor factor VArg$^{506}$→Gln is not impaired, indicating that the Arg$^{306}$ cleavage site is already available in intact factor V and that the increased rate of inactivation of factor Va versus V is the result of a more prominent exposure of Arg$^{506}$ after activation of factor V. The kinetics of activation and inactivation of factor V and factor Va are thus of great significance for the observed resistance of factor VaArg$^{506}$→Gln (26).

Factor Va in complex with factor Xa has been reported to be protected against inactivation by APC (28). This coupled to the structural similarity of APC and factor Xa and the similarity of interaction of both enzymes to the cofactor suggests that they compete for the same site (29). The rate of inactivation of factor Va is therefore dependent upon the concentration of formed Xa versus the concentration of formed APC.

Protein S is a vitamin K-dependent coagulation factor involved in the regulation of the anticoagulant activity of APC. [For a review on protein S see reference 30]. Protein S is thought to serve as a non-enzymatic cofactor for APC. In plasma, approximately 60% of protein S is completed to C4b-binding protein (C4BP), a component of the complement system and, when bound to C4BP, protein S is unable to function as a cofactor for APC (30). Protein S has been reported to neutralize the protective effect of factor Xa on the APC dependent inactivation of factor Va (31). Because only a 2-fold potentiation by protein S of the inactivation of factor Va by APC in the absence of factor Xa is observed, the deprotection by protein S of factor Va in the presence of factor Xa has been suggested as a possibly important physiological function of protein S. Other suggested functions of protein S include a direct inhibition of prothrombinase activity by protein S, independent of APC (32–34). This effect of protein S was shown to be very significant under conditions of flow and was hypothesized to result for a large part by the occupation of protein S of plant membranes via the high affinity membrane interaction of protein S, which blocks sites of assembly of the vitamin K dependent enzyme complexes. Although at the present time the physiological functions of protein S remains to be clarified, the numerous reports of protein S deficiency associated with familial thrombosis demonstrate the importance of protein S as a coagulation inhibitor (35,36). Rosing et al. (37) conclude in a recent report that protein S normalizes the inactivation of factor Va$^{LEIDEN}$ by APC, and hypothesize that this normalization by protein S may be the reason why only a relatively small percentage of the individuals with a factor V$^{LEIDEN}$ mutation develop thrombosis.

Recently an empirical model for the tissue factor pathway to thrombin using purified coagulation factors (38) has been developed as well as a theoretical mathematical model (39) which simulates thrombin formation based upon known kinetic constants for the essential activation reactions thought to be involved in blood coagulation. The empirical model has been expanded to include the stoichiometric inhibitors TFPI and AT-III (40) and the dynamic protein C pathway (41). It was found that thrombin generation initiated by low pM concentrations of factor VIIa·TF was effectively neutralized by the combination of TFPI and the protein C pathway after the initial generation of a limited amount of thrombin. At physiological concentrations of TFPI and protein C the effectiveness of this combination of inhibitors to inhibit the reaction was shown to be governed by the relative concentrations of thrombomodulin and factor VIIa·TF. Of interest here is that this combination of inhibitors are both produced by and are present on the endothelium in vivo; thrombomodulin as a transmembrane protein constitutively expressed on the luminal side of the endothelial cells (12) and full-length TFPI bound to endothelium exposed heparan sulfate-like glycosaminoglycans (42–45).

There is a need in the art for methods to identify those at risk due to a factor V$^{LEIDEN}$ mutation. There is also a need in the art for prophylactic methods to reduce that risk.

SUMMARY OF THE INVENTION

The present invention provides the art with a method of selecting persons having an elevated risk for thromboses. Plasma TFPI level of a person are measured. It is also determined if the person carries a Factor V$^{LEIDEN}$ allele. If the person has a lower than average plasma TFPI level and a Factor V$^{LEIDEN}$ allele, the person is at elevated risk for thrombosis relative to the general population.

Also provided by the present invention is a method of reducing the risk of thrombosis in a person who carries a Factor V$^{LEIDEN}$ allele. An amount of TFPI or active fragment thereof is administered to the person. The amount is sufficient to achieve plasma levels of TFPI activity which are higher than average.

These and other embodiments of the invention provide the art with diagnostic and prophylactic methods useful in management of persons having a Factor V$^{LEIDEN}$ mutation.

BRIEF DESCRIPTION OF THE DRAWINGS

FIG. 2 Generation and cleavage of the factor V heavy chain of normal factor V (panel 4) and factor V$^{LEIDEN}$ (panel B) of SDS-quenched samples of the experiment shown in FIG. 1 of the reactions in the presence of the protein C pathway. Samples run on 4–12% polyacrylamide gradient gels under nonreducing conditions, transferred to nitrocellulose and immunoblotted with a-HFV-6 as described under methods. a-HFV-6 recognizes an epitope on the heavy chain between residues 307–506 (50). Products formed are the same as observed in isolated systems, products formed are consistent with the lack of the cleavage site for APC at residue 506 in factor V$^{LEIDEN}$.

Figure 1:
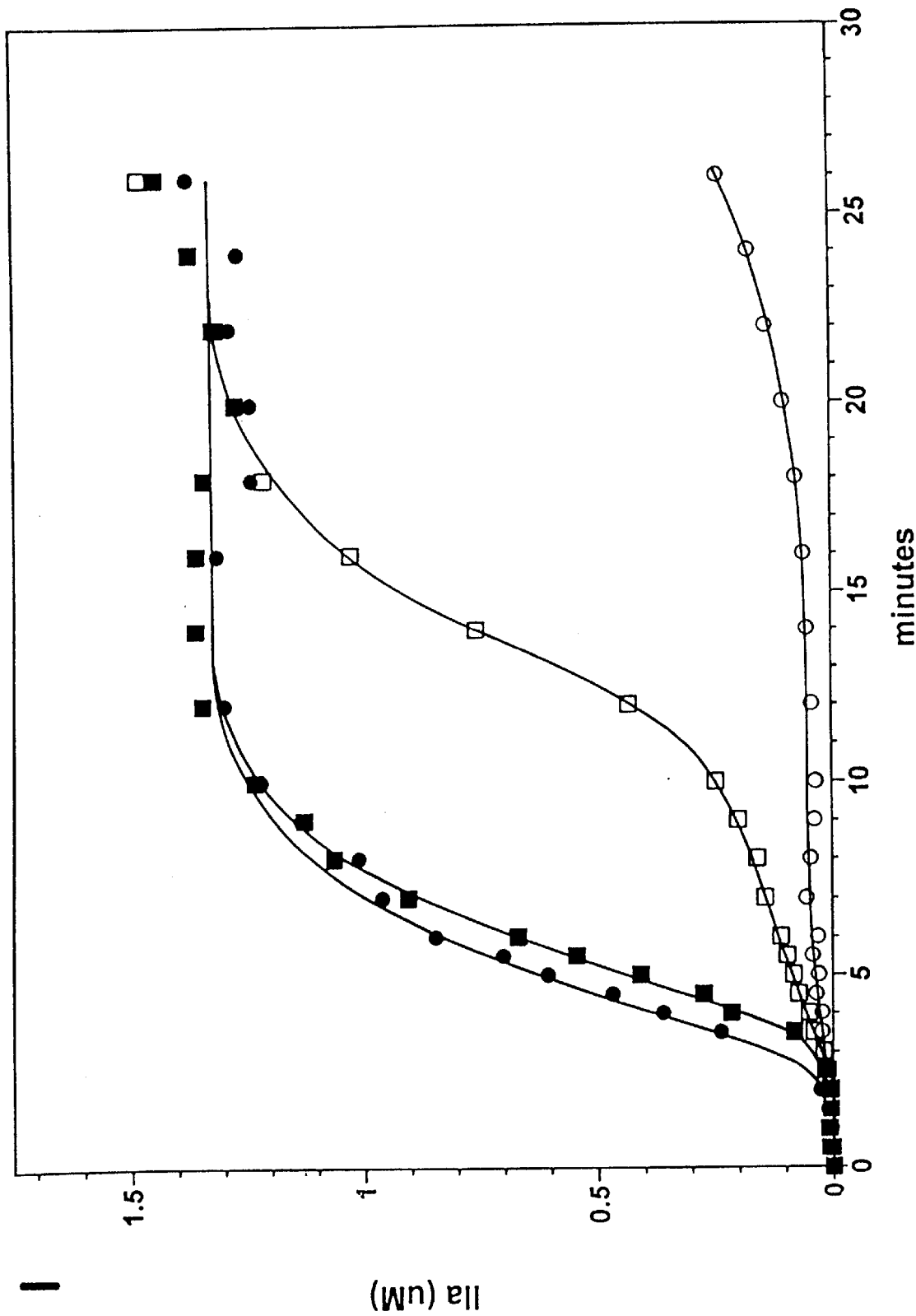
FIG. 1. Effect of the factor V$^{LEIDEN}$ mutation (squares) on thrombin generation in the reconstituted tissue factor pathway to thrombin in the absence (filled symbols) and presence (open symbols) of the protein C pathway (65 nM protein C+10 nM thrombomodulin). Thrombin generation is initiated with 1.25 pM factor VIIa·TF in the presence of 2.5 nM TFPI as described under Methods. Thrombin generation by normal factor V (circles) is effectively shut down by the protein C pathway in the presence of TFPI as described (40). Thrombin generation by factor V$^{LEIDEN}$ continues in the presence of the protein C pathway (open squares) and still results in the quantitative conversion of prothrombin into thrombin.

is still effectively inhibited by the protein pathway (65 nM protein C, 10 nM thrombomodulin, 300 nM protein S, open symbols) at 1.25 nM TFPI while thrombin generation by factor $V^{LEIDEN}$ (squares) is not inhibited by the protein C pathway and 1.25 nM TFPI. Closed symbols represent the controls in the absence of the protein C pathway.

DETAILED DESCRIPTION OF THE PREFERRED EMBODIMENTS

It has now been found that lower than average plasma TFPI levels and a Factor $V^{LEIDEN}$ mutation cause a person to be at elevated risk for thrombosis, relative to the general population. Thus it is desirable that TFPI levels be artificially elevated to at least the average plasma level to reduce risk of thromobosis.

TFPI can be administered by any means known in the art, including by infusion pump, orally, by injections, intravenous or otherwise, subcutaneously, etc.

TFPI can be formulated according to any means known in the art. However, a liquid formulation is preferred. TFPI can be formulated in 150 mM NaCl and 20 mM NaPO$_4$ at pH 7.2. However, TFPI may be formulated at different concentrations or using different formulants. For example, these formulants may include oils, polymers, vitamins, carbohydrates, amino acids, salts, buffers, albumin, surfactants, or bulking agents. Preferably carbohydrates include sugar or sugar alcohols such as mono, di, or polysaccharides, or water soluble glucans. The saccharides or glucans can include fructose, dextrose, lactose, glucose, mannose, sorbose, xylose, maltose, sucrose, dextran, pullulan, dextrin, alpha and beta cyclodextrin, soluble starch, hydroxethyl starch and carboxymethylcellulose, or mixtures thereof. Sucrose is most preferred. Sugar alcohol is defined as a $C_4$ to $C_8$ hydrocarbon having an —OH group and includes galactitol, inositol, mannitol, xylitol, sorbitol, glycerol, and arabitol. Mannitol is most preferred. These sugars or sugar alcohols mentioned above may be used individually or in combination. There is no fixed limit to amount used as long as the sugar or sugar alcohol is soluble in the aqueous preparation. Preferably, the sugar or sugar alcohol concentration is between 1.0 w/v % and 7.0 w/v %, more preferable between 2.0 and 6.0 w/v %. Preferably amino acids include levorotary (L) forms of carnitine, arginine, and betaine; however, other amino acids may be added. Preferred polymers include polyvinylpyrrolidone (PVP) with an average molecular weight between 2,000 and 3,000, or polyethylene glycol (PEG) with an average molecular weight between 3,000 and 5,000. It is also preferred to use a buffer in the composition to minimize pH changes in the solution before lyophilization or after reconstitution. Most any physiological buffer may be used, but citrate, phosphate, succinate, and glutamate buffers or mixtures thereof are preferred. Preferably, the concentration is from 0.01 to 0.3 molar. Surfactants that can be added to the formulation are shown in EP Nos. 270,799 and 268,110.

Additionally, TFPI can be chemically modified by covalent conjugation to a polymer to increase its circulating half-life, for example. Preferred polymers, and methods to attach them to peptides, are shown in U.S. Pat. Nos. 4,766, 106, 4,179,337, 4,495,285, and 4,609,546 which are all hereby incorporated by reference in their entireties. Preferred polymers are polyoxyethylated polyols and polyethylene glycol (PEG). PEG is soluble in water at room temperature and has the general formula: R(O—CH$_2$—CH$_2$)O—R where R can be hydrogen, or a protective group such as an alkyl or alkanol group. Preferably, the protective group has between 1 and 8 carbons, more preferably it is methyl. The symbol n is a positive integer, preferably between 1 and 1,000, more preferably between 2 and 500. The PEG has a preferred average molecular weight between 1000 and 40,000, more preferably between 2000 and 20,000, most preferably between 3,000 and 12,000. Preferably, PEG has at least one hydroxy group, more preferably it is a terminal hydroxy group. It is this hydroxy group which is preferably activated to react with a free amino group on the inhibitor. However, it will be understood that the type and amount of the reactive groups may be varied to achieve a covalently conjugated PEG/IL-2 of the present invention.

Water soluble polyoxyethylated polyols are also useful in the present invention. They include polyoxyethylated sorbitol polyoxyethylated glucose, polyoxyethylated glycerol (POG), etc. POG is preferred. One reason is because the glycerol backbone of polyoxyethylated glycerol is the same backbone occurring naturally in, for example, animals and humans in mono-, di-, triglycerides. Therefore, this branching would not necessarily be seen as a foreign agent in the body. The POG has a preferred molecular weight in the same range as PEG. The structure for POG is shown in Knauf et al., 1988, *J. Bio. Chem.* 263:15064–15070, and a discussion of POG/IL-2 conjugates is found in U.S. Pat. No. 4,766,106, both of which are hereby incorporated by reference in their entireties.

Injectable preparations, for example, sterile injectable aqueous or oleaginous suspensions may be formulated according to the known art using suitable dispersing or wetting agents and suspending agents. The sterile injectable preparation may also be a sterile injectable solution or suspension in a nontoxic parenterally acceptable diluent or solvent, for example, as a solution in water. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono or diglycerides. In addition, fatty acids such as oleic acid find use in the preparation of injectables. A preferred injectable preparation solution is TFPI in an aqueous solution of 150 mM sodium chloride and 20 mM sodium phosphate.

After the liquid pharmaceutical composition is prepared, it is preferably lyophilized to prevent degradation and to preserve sterility. Methods for lyophilizing liquid compositions are known to those of ordinary skill in the art. Just prior to use, the composition may be reconstituted with a sterile diluent (Ringer's solution, distilled water, or sterile saline, for example) which may include additional ingredients. Upon reconstitution, the composition is preferably administered to subjects using those methods that are known to those skilled in the art.

Dosage of TFPI to be administered as a total daily dose in single or divided doses may be in amounts, for example, from about 2 to about 50 mg/kg body weight daily and more usually 4 to 20 mg/kg, preferably, from about 6 to about 10 mg/kg. Dosage unit compositions may contain such amounts or submultiples thereof to make up the daily dose. Lower amounts may be useful for prophylactic or other purposes, for example, from 1 μg/kg to 2 mg/kg. The amount of active ingredient that may be combined with the carrier materials to produce a single dosage form will vary depending upon the patient treated and the particular mode of administration.

The dosage regimen is selected in accordance with a variety of factors, including the type, age, weight, sex, diet and medical condition of the patient, the severity of the condition, the route of administration, pharmacological considerations such as the activity, efficacy, pharmacokinetic and toxicology profiles, whether a drug delivery system is utilized and whether the compound is administered as part of a drug combination. Thus, the dosage regimen actually employed may vary widely and therefore may deviate from the preferred dosage regimen set forth above.

The mean concentration of TFPI in normal plasma is 89 ng/ml or 2.25 nmol/l. The 95% range in a population of normal adults is from 53 ng/ml to 142 ng/ml. Novotny et al., 1991, *Blood*, 78:387–393. A report by Bajaj et al., 1987, *J. Clin. Invest.*, 79:1874–1878, suggests that TFPI is synthesized in liver and endothelial cells and is consumed during DIC in patients. Specifically, TFPI values in the plasma of 15 healthy volunteers ranged from 72 to 142 ng/ml with a mean of 101 ng/ml. Interestingly, TFPI levels of 10 patients with DIC were 57±30 ng/ml (p<0.001). In contrast, TFPI levels of 12 patients with hepatocellular disease were a mean of 107±33, i.e., similar to normal. Sandset et al., 1989, *J. Internal Med.*, 225:311–316, monitored TFPI plasma levels during a 7-day observation period from patients with pneumonia (n=13), and in stroke patients with infarction (n=9), and haemorrhage (n=9). In pneumonia patients, TFPI showed a weak but not significant increase in the recovery period (p=0.068). In cerebral haemorrhage patients, TFPI levels did not consistently change, while in cerebral infarction patients, an increase in TFPI levels was observed from day 1 to day 2 (p<0.05). This latter effect was most probably due to release of tissue bound TFPI by heparin and thus, was only observed in heparin-treated patients.

Plasma levels of TFPI can be measured according to any method known in the art. Immunological assays can be used, as well as biochemical assays. See, for example, Broze et al., *Blood* 71:335, 1988.

Determination of a Factor $V^{LEIDEN}$ allele can also be performed by methods known in the art. The presence of the mutation can be determined in a patient's genome by any analytic means known in the art. For example, sequencing of PCR-amplified DNA or hybridization to mutation-specific probes can be used to identify such alleles. In addition, biochemical assays demonstrating activated protein C (APC) resistance can be used.

Fragments and variants of TFPI can also be used. For example, fragments which comprise the first and or second Kunitz-domain are desirable. These domains consist of amino acids 47–117 and 118–188, respectively. It may be desirable that all or part of the third domain which consists of amino acids 210–280 be deleted. Such deletions reduce the heparin-binding ability of the TFPI molecules.

Three truncated versions of TFPI have been produced from *E. coli*. These are ala-TFPI-1–160; ala-TFPI-13–161, and ala-TFPI-22–150. These derivatives have production advantages and favorable solubility characteristics compared to full-length ala-TFPI (ala-TFPI). The derivatives are produced at levels approximately 7–10 fold higher than full-length ala-TFPI. Solubility of the derivatives in a physiological buffer, e.g., phosphate buffered saline, is about 40 to 80-fold higher than full-length ala-TFPI. In addition, the clearance rate appears slower for at least one of the derivatives relative to the full-length form. All three forms are active in factor Xa-dependent inhibition of factor VIIa/ tissure factor activity. Ala-TFPI-1–160 was tested in a baboon model of sepsis and was found to promote survival. Five of eight animals treated with the fragment survived to the 7 day endpoint, while none of five untreated control baboons survived.

To retain the TFPI activity, analogues and fragments should at least contain the N-terminal sequence including the first and second Kunitz domain. Thus, the TFPI analogues according to the present invention should at least contain the amino acid sequence from amino acid number 25 to amino acid number 148 of native TFPI (see FIGS. 1 and 2).

Heparin binding capacity is lost when the sequence from amino acid residue number 162 to amino acid residue number 275 is deleted from the TFPI molecule. Therefore the heparin binding domain is situated in this part of the TFPI molecule. It is assumed that the heparin binding domain comprises at least a region from Arg246 to Lys265 near the C-terminal end of the TFPI molecule being rich in positively charged amino acid residues.

Preferred TFPI analogues and fragments are those in which one or more amino acid residues have been deleted in the native TFPI molecule from amino acid residue Glu148 to the C-terminal Met276. More specifically, preferred analogues and fragments have one or more amino acid residues in the sequence from Arg246 to Lys275 has been deleted.

Examples of TFPI analogues and fragments according to the present invention are:
(Aspl-Thr255)-TFPI
(Aspl-Ile253)-TFPI
(Aspl-Lys249)-TFPI
(Aspl-Ser248)-TFPI
(Aspl-Lys240)-TFPI
(Aspl-Glu234)-TFPI
(Aspl-Trp188)-TFPI
(Aspl-Asn164)-TFPI
(Aspl-Thr161)-TFPI
(Aspl-Asp149)-TFPI
(Aspl-Glu148)-TFPI
Ser-(Aspl-Thr255)-TFPI
Ser-(Aspl-Ile253)-TFPI
Ser-(Aspl-Lys249)-TFPI
Ser-(Aspl-Ser248)-TFPI
Ser-(Aspl-Lys240)-TFPI
Ser-(Aspl-Glu234)-TFPI
Ser-(Aspl-Trp188)-TFPI
Ser-(Aspl-Asn164)-TFPI
Ser-(Aspl-Thr161)-TFPI
Ser-(Aspl-Asp149)-TFPI
Ser-(Aspl-Glu148)-TFPI
(Glu15 -Thr255)-TFPI
(Glu15-Ile253)-TFPI
(Glu15-Lys249)-TFPI
(Glu15-Ser248)-TFPI
(Glu15-Lys240)-TFPI
(Glu15-Glu234)-TFPI
(Glu15-Trp188)-TFPI
(Glu15-Asn164)-TFPI
(Glu15-Thr161)-TFPI
(Glu15-Asp149)-TFPI
(Glu15-Glu148)-TFPI
Ser-(Glu15-Thr255)-TFPI
Ser-(Glu15-Ile253)-TFPI
Ser-(Glu15-Lys249)-TFPI
Ser-(Glu15-Ser248)-TFPI
Ser-(Glu15-Lys240)-TFPI
Ser-(Glu15-Glu234)-TFPI
Ser-(Glu15-Trp188)-TFPI
Ser-(Glu15-Asn164)-TFPI
Ser-(Glu15-Thr161)-TFPI
Ser-(Glu15-Asp149)-TFPI
Ser-(Glu15-Glu148)-TFPI (Ser24-Thr255)-TFPI
(Ser24-Ile253)-TFPI
(Ser24-Lys249)-TFPI
(Ser24-Ser248)-TFPI
(Ser24-Lys240)-TFPI
(Ser24-Glu234)-TFPI
(Ser24-Trp188)-TFPI
(Ser24-Asn164)-TFPI
(Ser24-Thr161)-TFPI
(Ser24-Asp149)-TFPI
(Ser24-Glu148)-TFPI
(Asp1-Thr255)-(Ile266-Met276)-TFPI
(Asp1-Ile253)-(Ile266-Met276)-TFPI
(Asp1-Ser248)-(Ile266-Met276)-TFPI
(Asp1-Gln245)-(Ile266-Met276)-TFPI
(Asp1-Thr255)-(Val264-Met276)-TFPI
(Asp1-Ile253)-(Val264-Met276)-TFPI
(Asp1-Ser248)-(Val264-Met276)-TFPI
(Asp1-Glu245)-(Val264-Met276)-TFPI
(Asp1-Thr255)-(Glu262-Met276)-TFPI
(Asp1-Ile253)-(Glu262-Met276)-TFPI
(Asp1-Ser248)-(Glu262-Met276)-TFPI
(Asp1-Glu245)-(Glu262-Met276)-TFPI
(Ser-Asp1-Thr255)-(Ile266-Met276)-TFPI
(Ser-Asp1-Ile253)-(Ile266-Met276)-TFPI
(Ser-Asp1-Ser248)-(Ile266-Met276)-TFPI
(Ser-Asp1-Gln245)-(Ile266-Met276)-TFPI
(Ser-Asp1-Thr255)-(Val264-Met276)-TFPI
(Ser-Asp1-Ile253)-(Val264-Met276)-TFPI
(Ser-Asp1-Ser248)-(Val264-Met276)-TFPI
(Ser-Asp1-Glu245)-(Val264-Met276)-TFPI
(Ser-Asp1-Thr255)-(Glu262-Met276)-TFPI
(Ser-Asp1-Ile253)-(Glu262-Met276)-TFPI
(Ser-Asp1-Ser248)-(Glu262-Met276)-TFPI
(Ser-Asp1-Glu245)-(Glu262-Met276)-TFPI In addition to the described deletions in the TFPI molecule, certain amino acid residues of native TFPI may also be replaced by another naturally occurring amino acid residue. Desirably these are conservative amino acid changes. More desirably these are in portions of TFPI not critical for activity. The TFPI analogues may also advantageously contain a Ser residue as the N-terminal residue. This is necessary if a signal sequence is used requiring an N-terminal Ser in the mature protein as a recognition site for cleavage. Thus, the N-terminal in the TFPI molecule may be replaced by a Ser or an additional Ser may be inserted adjacent to the original N-Terminal residue. Also the potential glycosylation sites at Asn167 and Asn238 may be substituted by another amino acid residue to avoid glycosylation.

The following examples are provided for exemplification purposes only and are not intended to limit the scope of the invention which has been described in broad terms above.

EXAMPLES

Materials and Methods

Phosphatidylserine (PS) from bovine brain, phosphatidylcholine (PC) from egg yolk and Hepes were purchased from Sigma. D-Phenylalanyl-L-arginine chloromethyl ketone (FPR-ck) was a gift from Dr. R. Jenny, Haemologic Technologies Inc. (Essex Jct, Vt) Spectrozyme TH was purchased from American Diagnostica, Inc. Q-Sepharose FF was obtained from Pharmacia. All other reagents were of analytical grade.

Human coagulation factors X, IX and prothrombin were isolated from fresh frozen plasma using the general methods of Bajaj et al (46). Factor X and factor IX were passed over an anti-prothrombin immunoaffinity column in 20 mM Tris, 150 mM NaCl, 1 mM benzamidine pH 7.4 (TBS/benz) and concentrated on Q-Sepharose FF columns of 3 ml. Traces of factor VII were removed by washing the Q-Sepharose columns with 10 mM $CaCl_2$, 50 mM NaCl, 20 mM Tris, 1 mM benzamidine pH 7.4. After the columns were washed with buffer without $CaCl_2$ factor X and factor IX were eluted with 1 M TBS/benz. Prothrombin was passed over anti-factor X and anti-protein C immunoaffinity columns, concentrated and depleted of traces of factor VII using Q-Sepharose as described for factor X and factor IX. Prothrombin was eluted from the Q-Sepharose column with 20 mM $CaCl_2$, 150 mM NaCl, 20 mM Tris, 1 mM benzamidine. To inhibit traces of active enzymes in the zymogen preparations the factor X, factor IX and prothrombin preparations were sequentially treated with 1 mM diisopropylphosphorofluoridate (DFP) and 10 uM FPR-ck respectively. After treatments with either DFP or FPR-ck the proteins were extensively dialyzed in 20 mM Tris, 150 mM NaCl pH 7.4 (TBS) to remove free DFP or FPR-ck After the last dialysis aliquots were frozen in liquid nitrogen and stored at $-80°$ C.

Protein C was purified by heparin-Sepharose and immuno-chromatography from the protein C-pool eluting in the NaCl gradient of the DEAE-Sepharose column involved in the purification of the vitamin-K dependent clotting factors. Protein S was a gift from Dr. R. Jenny, Hematologic Technologies Inc. (Essex Jct, Vt). Protein S appeared as a single band of Mr=69,000 on SDS-PAGE under non-reducing conditions. Approximately 10% of the protein S was cleaved in its thrombin sensitive region as was judged by the appearance of a Mr=65,000 band under reducing conditions.

Human factor V was isolated by using the methods of Nesheim et al (47). Factor $VArg^{506} \rightarrow Gln$ was purified from plasma of a patient which is homozygous for the factor $V^{LEIDEN}$ mutation as described (26). Recombinant factor VIII and recombinant tissue factor were provided as a gift from Drs. Shu Len Liu and Roger Lundblad, Hyland division, Baxter Healthcare Corp. Recombinant human coagulation factor VIIa was purchased from NOVO pharmaceuticals. Recombinant soluble thrombomodulin (Solulin) was provided as a gift from Dr. J. Morser, Berlex. Recombinant full-length TFPI produced in *E. coli* was provided as a gift from Dr. K. Johnson, Chiron Corp.

Coagulation Factor Activation Experiments

TF (0.5 nM) was relipidated essentially as described previously (38) into 400 $\mu$M 75% phosphatidylcholine 25% phosphatidylserine vesicles, for 30 minutes at 37° C. in 20 mM Hepes, 150 mM NaCl, 2 mM $CaCl_2$ pH 7.4 (Hepes/$Ca^{2+}$). The relipidated TF was incubated with factor VIIa for 20 minutes at 37° C. to allow factor VIIa·TF complex formation. After that factor V and factor VIII were added to the factor VIIa·TF solution and immediately thereafter the reaction was started by adding a solution containing factor X, factor IX and prothrombin prepared in Hepes/$Ca^{2+}$.

The final concentrations of the proteins in the reaction are 160 nM factor X, 90 nM factor IX, 0.7 nM factor VIII, 20 nM factor V, 1.4 $\mu$M prothrombin which are all at or near the mean normal plasma concentration of the respective coagulation factor. The factor VIIa·TF concentration was limited by the factor VIIa concentration, (1.25 pM). The final concentration of TF was 0.25 nM. When added to the reaction TFPI, protein C or protein S were added to the mixture of X, IX and prothrombin. Thrombomodulin was added to the factor VIIa·TF mixture. After starting the reaction, aliquots were withdrawn at various times from the reaction mixture and quenched in either 20 mM EDTA/TBS pH 7.4 to assay for thrombin formation, or in 2% SDS, 0.06 M Tris, 10% glycerol, 0.1% bromophenol Blue pH 6.8 for SDS-PAGE and immunoblotting. Assays for thrombin activity were performed using the chromogenic substrate Spectrozyme TH. The hydrolysis of the substrate was monitored by the change in absorbance at 405 nm using a Molecular Devices $V_{max}$ spectrophotometer. Thrombin generation was calculated from a standard curve prepared by serial dilution of a-thrombin. The samples quenched in SDS were subjected to SDS-PAGE under nonreducing conditions on 4–12% polyacrylamide gels as generally described by Laemmli (48). Following SDS-PAGE the proteins were transferred to nitrocellulose membranes for immunoblot analysis using general techniques described by Towbin et al (49). Membranes were blocked for nonspecific binding with 5% nonfat dry milk in 0.05% Tween TBS and incubated for 1.5 hour with monoclonal antibody αHFV-6. This antibody recognizes an epitope on the heavy chain of factor V between residues 307–506 (49). This fragment is a final product of factor Va cleavage by APC. The products of factor V recognized by this antibody were visualized using peroxidase conjugated horse anti-mouse IgG and the Renaissance chemiluminescent reagent (Dupont, Boston, Mass.).

After that the membranes were washed with 0.5 M NaCl, 0.1 M glycine, pH 2.7 to remove bound antibodies. The washed membranes were blocked again with 5% nonfat milk and probed for prothrombin activation products using a polyclonal burro anti-prethrombin-1 antibody as described (38).

EXAMPLE 1

Effect of the Factor $V^{LEIDEN}$ Mutation on Factor VIIa·TF Triggered Thrombin Generation in the Presence and the Absence of the Protein C Pathway The effect of the $Arg^{506} \rightarrow Gln$ substitution in factor $V^{LEIDEN}$, leading to a partially APC resistant cofactor, was evaluated in the reconstituted tissue factor pathway to thrombin because a) all components are well characterized and reconstituted with full knowledge of their concentration, which excludes effects of unknown proteins which may influence the outcome of plasma based experiments, b) the mixture of components can easily be varied allowing reconstitution of possible combined disorders and c) the reaction is started with zymogens and procofactors, thus providing the physiological mixture in which the rate at which the active products are formed, inactivated or stabilized by feed-forward, feed-backward or protective mechanisms as described in the introduction, is decisive in achieving a threshold for thrombin generation.

The effect of the $Arg^{506} \rightarrow Gln$ substitution in factor $V^{LEIDEN}$ was studied in the reconstituted model using purified factor $V^{LEIDEN}$. Thrombin generation was initiated with 1.25 pM factor VIIa·TF in the presence of the approximate physiological concentration of TFPI (2.5 nM). When added, the protein C pathway was reconstituted by adding protein C (65 nM) and thrombomodulin (10 nM) to the system. Thrombin generation in the absence of the protein C pathway occurred after an initial lag phase of 2.5 minutes after which prothrombin was converted into thrombin at 3 nM/sec during the following propagation phase. This thrombin generation profile was essentially the same when thrombin generation was catalyzed by either normal factor V or factor $VArg^{506} \rightarrow Gln$ (FIG. 1, closed symbols). In the presence of the protein C pathway components, thrombin generation occurred after the same lag time of 2.5 minutes, albeit at a reduced rate. At 5 minutes, thrombin generation was terminated after $\leq 25$ nM thrombin was produced. Thus, at this factor VIIa·TF concentration the protein C pathway completely eliminated the propagation phase of the reaction after a limited amount of thrombin was formed (FIG. 1, open circles).

The reaction catalyzed by factor $V^{LEIDEN}$ in the presence of thrombomodulin and protein C also occurred at a lag time of 2.5 minutes, however thrombin generation was not attenuated by the protein C pathway and continued initially at a rate of 0.44 nM/sec (FIG. 1, open squares). After 10 minutes the rate of thrombin generation by factor $VArg^{506} \rightarrow Gln$ started to increase; ultimately increasing to the maximal rate observed in the absence of protein C/thrombomodulin. Prothrombin was quantitatively converted to thrombin (1.4 µM) after 16 minutes. The results show that factor VIIa·TF triggered thrombin, generation catalyzed by factor $V^{LEIDEN}$ can be surpressed by the protein C pathway in combination with TFPI, however the protein C pathway fails to completely eliminate the propagation phase catalyzed by factor $V^{LEIDEN}$ under these conditions. Since in the model there is the potential to activate 65 nM protein C, this shows the incapability of the accumulating levels of APC to fully inactivate factor $Va^{LEIDEN}$ in the reaction. Analyses of the activation and inactivation of factor V by immunoblotting with monoclonal antibody αHFV-6 (49), showed that all factor V was cleaved during the lag phase of thrombin generation for both factor V species, i.e. in the first 90 seconds of the reaction (FIG. 2). No reactive intermediate is observed of a molecular weight of Mr=280,000, meaning that there is no significant direct inactivation of intact factor V by cleavage of the procofactors at $Arg^{306}$ (26,27). In the absence of protein C/thrombomodulin the factor Va heavy chain is stable throughout the propagation phase of thrombin generation (data not shown)(38,41). In the presence of 65 nM protein C and 10 nM thrombomodulin (FIG. 2A) inactivation of normal Va is already observed during the initiation phase of the reaction (90 seconds) by the appearance of products which result from cleavage at $Arg^{506}$, as indicated by the appearance of the Mr=75,000 band which is composed of residues 1–506 of the factor Va heavy chain. Subsequent cleavage at $Arg^{306}$ gives rise to a Mr=30,000 reactive band consisting of residues 307–506 of the factor Va heavy chain (FIG. 2a). By 300 seconds most of the heavy chain is degraded by APC, yielding the 307–506 fragment. Cleavage at $Arg^{306}$ has been reported to be associated with complete loss of cofactor activity. This is consistent with the complete attenuation of prothrombinase activity at 300 seconds (FIG. 1, open circles).

Figure 3:
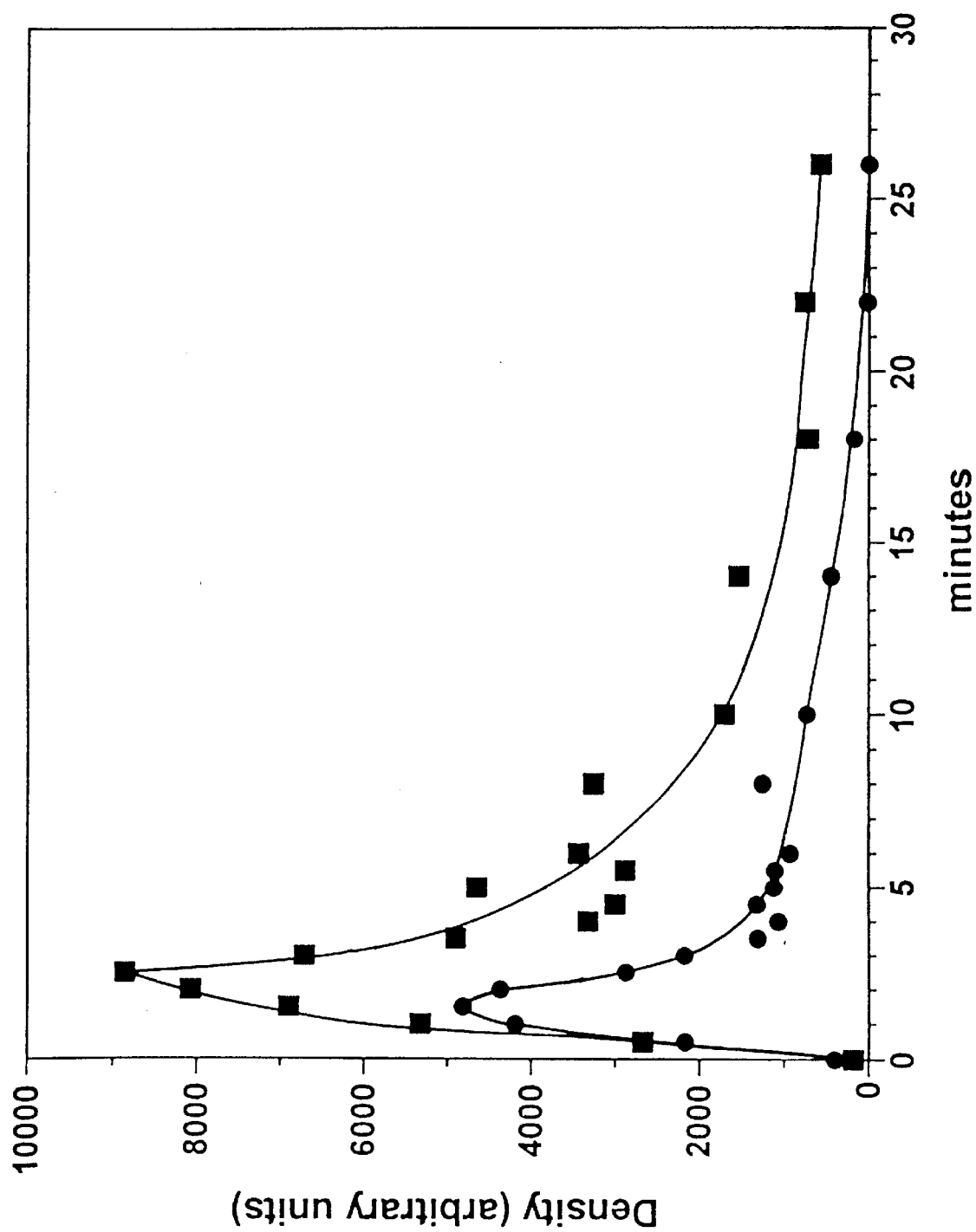
FIG. 3. Densitometry of the heavy chain of the immunoblot band in FIG. 2 of factor V and factor V$^{LEIDEN}$ during thrombin generation initiated by factor VIIa·TF and the protein C pathway. The heavy chain of factor V$^{LEIDEN}$ (■) reaches a higher optimal density and persist longer compared to the heavy chain of normal factor V (●), consistent with slower inactivation cleavages of activated factor V$^{LEIDEN}$ (26).

Inactivation of the heavy chain of factor $Va^{LEIDEN}$ in the presence of protein C/thrombomodulin (FIG. 2B) is observed after 150 seconds by cleavage at $Arg^{306}$ and Arg679 as indicated by the appearance of the Mr=48,000 reactive band (residues 307–709) and a Mr=45,000 reactive band (residues 307–679) consistent with the inability of APC to cleave this heavy chain at $Arg^{506}$ (26). Compared to normal factor V, the heavy chain of factor $V^{LEIDEN}$ is cleaved at a slower rate, and complete proteolysis of the heavy chain is only reached after 18 minutes. The remaining intact heavy chain and the 307–679 fragment are then cleaved by the abundant amounts of thrombin and/or factor Xa formed, resulting in Mr=85,000, 43,000 and 40,000 fragments (FIG. 2b). Densitometry of the factor V heavy chain bands (FIG. 3) for the experiments of FIG. 2A and B shows the higher cofactor concentrations reached in the case of factor $V^{LEIDEN}$ and the persistence of the factor $V^{LEIDEN}$ heavy chain in the presence of the protein C pathway when compared to normal factor V. The area under the heavy chain curve up to 20 minutes in the reaction revealed a 2.6-fold higher overall intensity of the factor $Va^{LEIDEN}$ heavy chain compared to the normal factor Va heavy chain during the reaction.

Figure 4A:
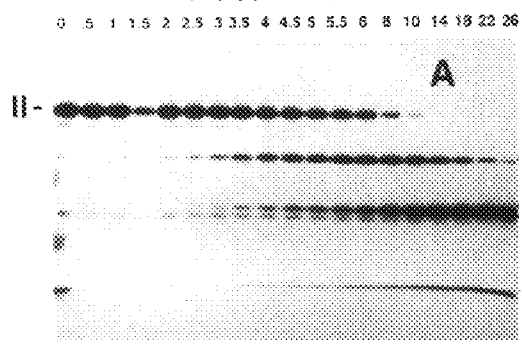
FIG. 4. Effect of the factor V$^{LEIDEN}$ mutation on prothrombin consumption as evaluated by immunoblotting for prothrombin and prothrombin products with a anti-human prethrombin-1-antibody after SDS-PAGE of SDS-quenched samples of the experiment shown in FIG. 1 on 4–12% gradient gels under non-reducing conditions. Prothrombin consumption by normal factor V prevented by the protein C pathway, while in the presence of the protein C pathway quantitative prothrombin consumption is still accomplished by factor V$^{LEIDEN}$. Panel A: normal factor V, B: factor V$^{LEIDEN}$, C: normal factor V+protein C pathway, D: factor V$^{LEIDEN}$+protein C pathway.
Figure 4B:
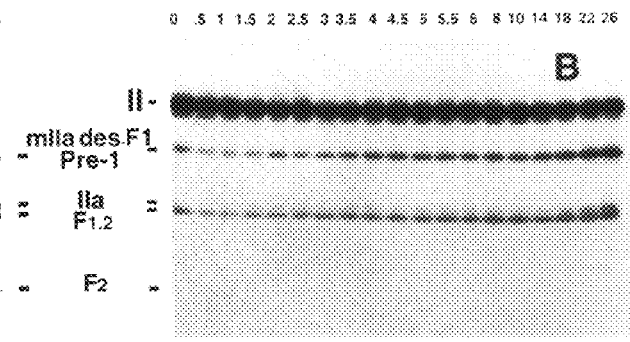
Figure 4C:
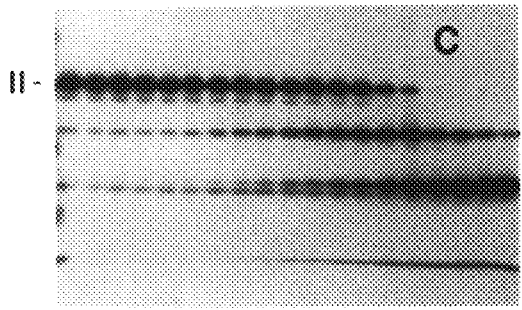
Figure 4D:
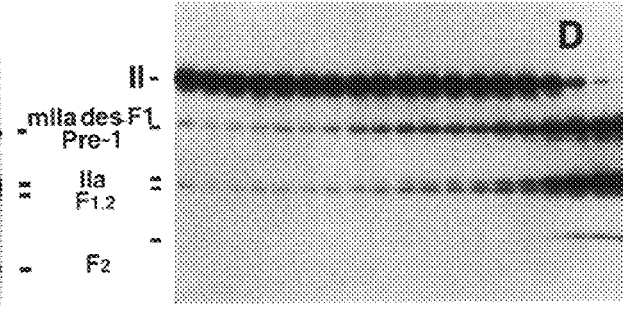

Analyses of prothrombin activation by immunoblotting show quantitative prothrombin consumption in the presence of both normal factor V and factor $V^{LEIDEN}$ in the absence of the protein C pathway (FIGS. 4A,B), coinciding with the appearance of 1.4 μM thrombin (FIG. 1, closed symbols). By activity assay 1.4 μM thrombin was measured when all prothrombin was consumed meaning that the product observed at Mr=50,000 is predominantly meizothrombindes-F1. Consistent with the attenuation of thrombin generation catalyzed by normal factor V in the presence of the protein C pathway, quantitative prothrombin consumption was not observed under these conditions (FIG. 4C), indicating that the observed inhibition of thrombin generation is caused by elimination of prothrombinase activity, and is not the result of conversion of prothrombin to prethrombin-1. In contrast, and consistent with the thrombin activity data, quantitative prothrombin consumption ultimately occurred but was delayed when the reaction was catalyzed by factor $V^{LEIDEN}$ in the presence of the protein C pathway (FIG. 4D).

EXAMPLE 2

Figure 5:
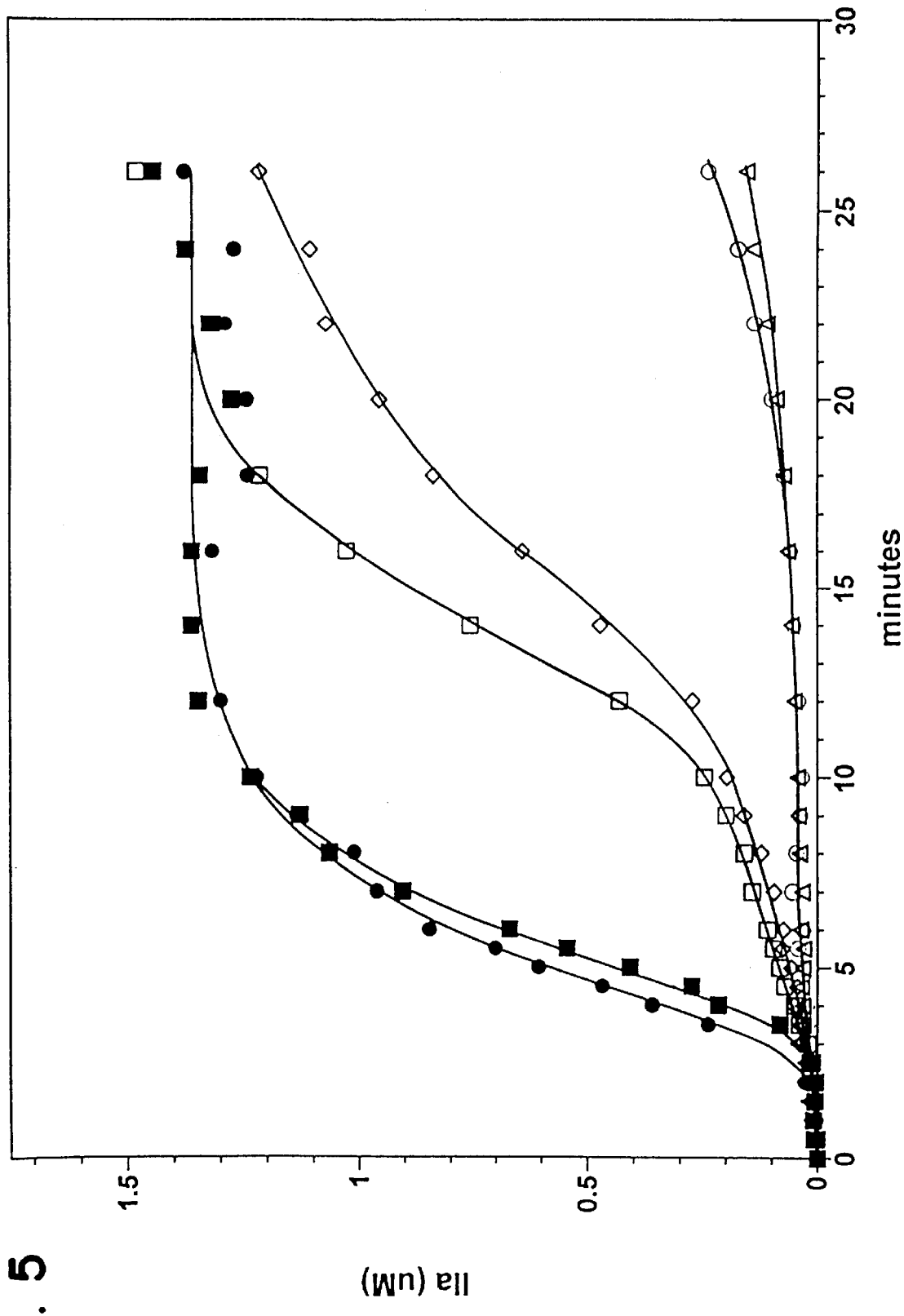
FIG. 5. Thrombin generation by normal factor V and factor V$^{LEIDEN}$ in the absence and presence of protein S (300 nM) and the protein C pathway (65 nM protein C+10 nM thrombomodulin). Thrombin generation is initiated by 1.25 pM factor VIIa·TF in the presence of 2.5 nM TFPI. Closed symbols are the controls in the absence of the protein C pathway components. Open symbols show the reactions in the presence of the protein C pathway. J: factor V, B: factor V$^{LEIDEN}$, E: factor V+protein C pathway, C: factor V+protein C pathway+protein S, G: factor V$^{LEIDEN}$+protein C pathway, A: factor V$^{LEIDEN}$+protein C pathway+protein S. Protein S does not significantly potentiate the protein C pathway in the presence of normal factor V (circles) or factor V$^{LEIDEN}$ (squares) as can be observed by the almost identical thrombin generation curves with and without protein S and the protein C pathway.

Effect of Protein S on Thrombin Generation Catalyzed by Factor V and Factor $V^{LEIDEN}$ in the Presence of the Protein C Pathway The effect of protein S, the reported cofactor of APC in the inactivation of factor Va and factor VIIIa, was studied on factor VIIa·TF (1.25 pM) initiated thrombin generation by adding 300 nM protein S (plasma concentration) to the combination TFPI/thrombomodulin/protein C(FIG. 5). Thrombin generation by normal factor V in the presence of the protein C pathway with and without protein S results in identical rates of thrombin generation ( FIG. 5, open circles and triangles). Thus under these conditions protein S does not significantly potentiate the inhibitory effect of the protein C pathway. Based upon the reported kcat/$K_m$ for the inactivation of factor Va by APC in the absence or presence of protein S this is to be expected (51). Protein S (300 nM) also failed to inhibit the observed initial rate of thrombin generation by factor $V^{LEIDEN}$ the presence of the protein C pathway components ( FIG. 5 open squares and diamonds). Similar to the thrombin generation by factor $V^{LEIDEN}$ in the presence of the protein C pathway without protein S, the rate of thrombin generation increased after 10 minutes in the presence of protein S and the other protein C pathway components. The rate of this secondary thrombin generation is slightly decreased (by approximately 30%) in the presence of protein S ( FIG. 5, open diamonds), but ultimately still results in the quantitative activation of prothrombin. The lack of a considerable effect of protein S on thrombin generation by factor $Va^{LEIDEN}$ in the presence of the protein C pathway shows that protein S does not play a descisive role in accelerating the APC dependent inactivation of factor $Va^{LEIDEN}$ when evaluated at the quasi-physiological conditions in the present model.

EXAMPLE 3

The Effect of Lowering the TFPI Concentration on Thrombin Generation Catalyzed by Factor $V^{LEIDEN}$ in the Presence of the Protein C Pathway and Protein S.

Figure 6:
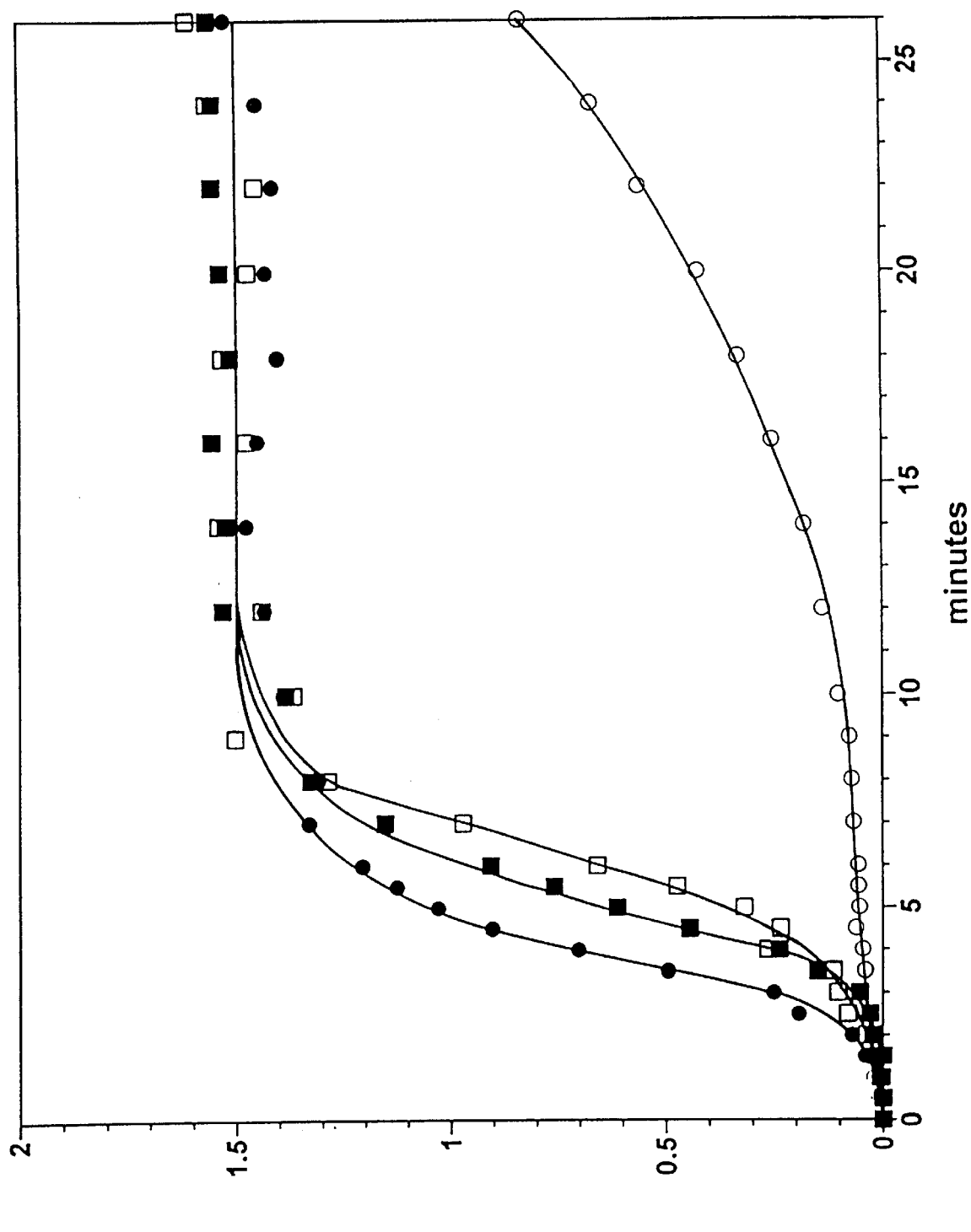
FIG. 6. Effect of the factor V$^{LEIDEN}$ mutation in the reconstituted model in the presence of 1.25 nM TFPI, a concentration of TFPI 50% lower than the TFPI used in FIG. 1 and FIG. 5. 1.25 nM TFPI resembles the concentration of TFPI at the lower limit of the normal plasma TFPI values observed in normal individuals. Initiating factor VIIa·TF is 1.25 pM. Thrombin generation by normal factor V (circles)

An experiment performed with TFPI concentrations of 1.25 TFPI, initiated by 1.25 pM factor VIIa·TF, is displayed in FIG. 6. This TFPI concentration represents 50% of the normal concentration in plasma, and represents the lower limit of TFPI plasma levels observed in healthy volunteers. In the presence of 1.25 nM TFPI, thrombin generation by normal factor V was initially terminated after the initiation phase by the protein C pathway (65 nM protein C, 10 nM thrombomodulin, 300 nM protein S) ( FIG. 6, open circles). However, thrombin generation started again after 10 minutes after a plateau phase of 5 minutes (FIG. 6, open circles). In contrast to the observed effective downregulation by the components of the protein C pathway of thrombin generation by normal factor V at a 50% reduced TFPI concentration, thrombin generation by factor $V^{LEIDEN}$ was not downregulated by protein C pathway constituents in the presence of 1.25 nM TFPI, and proceeded essentially at the same rate as in the absence of the components of the protein C pathway (FIG. 6, open and filled squares). This is of particular interest since thrombin generation under these conditions with normal factor V is still effectively slowed down by the protein C pathway in the complete absence of TFPI (41). These results indicate that relatively small differences in TFPI concentrations well within the range of "normal" TFPI plasma levels, may have large effects on thrombin generation in individuals with the factor $V^{LEIDEN}$ mutation under conditions were normally thrombin generation would be effectively downregulated by the protein C pathway.

Discussion

The activation pathways leading to thrombin formation after initiation by factor VIIa·TF have been studied extensively as isolated reactions, revealing the biochemical properties of the enzymes involved in this process. Recently we reported a system in which the pathway to thrombin was reconstituted by combining purified coagulation factors VIIa, X, IX, V, VIII and prothrombin with TF reconstituted in synthetic phospholipids (38). This model was extended with TFPI and the protein C pathway (41), a combination which is located on the endothelium in vivo. It was shown in the reconstituted model that the combined action of TFPI and the protein C pathway is very effective in shutting down the reaction after a limited initial amount of thrombin is formed. Consistent with thrombin·thrombomodulin dependent protein C activation, the small amounts of thrombin formed in and shortly after the lag phase activates protein C in quantities sufficient to eliminate further thrombin formation in the presence of TFPI. TFPI eliminates further factor Xa and factor IXa generation by the factor VIIa·TF complex, and further factor Xa generation by the IXa·VIIIa complex is probably eliminated by proteolysis of factor VIIIa by APC and thrombin (52–56) and dissociation of the polypeptides of factor VIIIa (57–59). The factor Xa that is generated is depleted from its cofactor Va also as the result of the action of APC. In respect to the physiological situation this suggests that combinations of TFPI, protein C and thrombomodulin are essential to prevent explosive thrombin formation after exposure of traces of TF.

The reconstituted coagulation system with TFPI, protein C and thrombomodulin allowed us to study the effect of the $Arg^{506} \rightarrow Gln$ substitution in factor $V^{LEIDEN}$ under conditions, which mimic the physiological coagulation pathway involving the feedforward and feedback reactions in this reaction (38,39).

The $Arg^{506} \rightarrow Gln$ substitution leads to a partial resistance against inactivation of factor Va by APC (26), which is the result of a slower inactivation of the cofactor because it lacks the cleavage site at $Arg^{506}$. In the absence of the $Arg^{506}$ APC cleavage site the inactivation of factor Va$^{LEIDEN}$ is dependent upon the relatively slow and phospholipid dependent initial cleavage at Arg$^{306}$ (27). In the reconstituted model thrombin generation initiated by factor VIIa·TF in the presence of either normal or Arg$^{506}$→Gln mutated factor V in the absence of protein C/thrombomodulin were essentially the same, consistent with the conclusion that the mutation does not impair the procoagulant function of the cofactor. In the presence of physiological concentrations of TFPI and protein C and 10 nM thrombomodulin, a combination of inhibitors which eliminates the propagation phase of thrombin generation catalyzed by normal factor V, initiated by 1.25 factor VIIa·TF, thrombin generation with factor V$^{LEIDEN}$, while inhibited by the protein C pathway, still resulted in the quantitative activation of prothrombin during the propagation phase. The persistant thrombin generation was associated with slower cleavage of the factor VaArg$^{506}$→Gln heavy chain when compared to the heavy chain of normal factor Va (FIG. 2). The products observed for the activation and inactivation of either normal factor V or factor V$^{LEIDEN}$ in the present study are not different from those products seen previously in isolated reactions and are consistent with the lack of the APC cleavage site at Arg$^{506}$ in factor V$^{LEIDEN}$. The inability of the protein C pathway to eliminate the propagation of factor VIIa·TF triggered thrombin generation by factor V$^{LEIDEN}$ in the presence of protein C/thrombomodulin and TFPI may explain the thrombotic effect of the resistance of the patients' Va molecule to APC.

Thrombin generation by normal factor V in the presence of the protein C pathway with and without protein S was identical, meaning that under these conditions protein S does not potentiate the inhibitory effect of the protein C pathway. Based upon previous studies with isolated reactions it was expected that protein S would become an important player by the elimination of the protection of factor Va by factor Xa from inactivation by APC. Under our experimental conditions protein S does not potentiate the inhibitory effect of the protein C pathway. The neutralization by protein S of the protecting effect of factor Xa on factor Va has been studied with nanomolar factor Xa concentrations which were equimolar or higher than factor Va (16). Based upon the rate of thrombin generation it can be concluded that only picomolar concentrations of factor Xa are formed under conditions thought to approach the physiologic (38). Only limited concentrations of factor Xa are generated and this trace of factor Xa is subject to direct inhibition by TFPI and its cofactor Va is depleted by APC. The complete activation of factor V during the initiation phase of the reaction results in the generation of 20 nM of factor Va heavy chain, and the protective effect of picomolar concentrations of factor Xa on the 20 nM of factor Va formed, appears to be insignificant under these conditions.

Protein S had no effect on the initial phase of thrombin generation by factor V$^{LEIDEN}$ in the presence of the protein C pathway, and reduced thrombin generation by 30% in the following propagation phase. The design of the reconstituted model, with all the involved proteins at their plasma concentrations involves the in situ generation of factor Xa, factor IXa, Va, VIIIa, thrombin and the thrombomodulin dependent in situ generation of activated protein C. This mimics the physiological appearance and disappearance of each protein species involved in the reaction. The rates at which procoagulant and anticoagulant processes proceed are decisive for the rate at which thrombin will be formed. The results obtained under these quasi-physiological, dynamic conditions suggest that the observed thrombotic events in protein S deficient individuals are not due to the proposed cofactor effect of protein S for APC. Our results do not support the suggested normalization by protein S of inactivation of factor Va$^{LEIDEN}$ by APC (37). The data presented are consistent with the hypothesis that thrombotic complications in protein S deficient individuals are the result of the lack of the APC independent inhibitory effect of protein S on prothrombinase activity (32–34). In control experiments no effect of protein S was observed on prothrombinase activity at the phospholipid concentrations (200 µM) used in the present reconstituted model.

The sensitivity of the APC regulation reaction to a relatively small change in the concentration of TFPI is intriguing. When experiments were performed with a 50% lower TFPI concentration of 1.25 nM, a concentration still considered to be within the normal range, thrombin generation by normal factor V was still shut down after the initiation phase by the protein C pathway. However at this concentration of TFPI the protein C pathway in the presence of protein S fails to extinguish thrombin generation catalyzed by factor V$^{LEIDEN}$. This is in contrast with the 85% inhibition of the initial rate of thrombin generation by the protein C pathway in the presence of 2.5 nM TFPI. The drastic effects on thrombin generation by factor V$^{LEIDEN}$ by variation of TFPI concentrations in the normal plasma range indicates that levels of TFPI in the lower range of normal values are a risk factor for thrombosis when combined with the Arg$^{506}$ →Gln mutation in factor V$^{LEIDEN}$. The inactivation of factor Va by APC proceeds by the relatively fast cleavage at Arg$^{506}$ and by cleavage at Arg679, these cleavages are accompanied by a relative small loss in cofactor activity when assayed at saturating levels of factor Xa, however cleavage at Arg$^{506}$/Arg$^{679}$ does result in significant loss of cofactor activity when assayed at low concentrations of factor Xa (60), indicating a diminished affinity of the factor Va/factor Xa interaction after cleavage at the Arg$^{506}$ and Arg$^{679}$ in factor Va.

In the reconstituted model, factor Xa and the generation of the factor Va light chain are the limiting factor in the generation of thrombin (41), and as such cleavage of factor Va at Arg$^{506}$ could possibly diminish the rate of thrombin generation because of the higher Kd of factor Va cleaved at Arg$^{506}$ for Xa. It is therefore also highly likely that the cleavage at Arg$^{506}$ is a major event in the regulation of thrombin generation by the protein C pathway in the presence of TFPI, which reduces the rate at which factor Xa is generated and inhibits factor Xa once formed.

It has also been found that in the presence of the protein C pathway the heavy chain of factor V becomes inactivated by APC before the generation of the light chain is completed. The slower generation of the light chain seems to provide a regulatory mechanism of factor Va activity which allows APC to prevent the generation of the full potential of factor Va cofactor activity by cleavage of the heavy chain. Generation of the light chain of factor Va is reported to be essential when cofactor activity is tested in a clotting assay or in a prothrombinase assay using low factor Xa concentrations (61,62). This means that the persistance of the heavy chain of factor V$^{LEIDEN}$ in the presence of the protein C pathway results in higher prothrombinase activity because of higher and persistant levels of the heavy chain following cleavage at Arg709, associated with increasing concentrations of light chain as a consequence of cleavage at 1545 to form higher levels of fully active factor Va.

The principles, preferred embodiments and modes of operation of the present invention have been described in the foregoing specification. The invention which is intended to be protected herein, however, is not to be construed as limited to the particular forms disclosed, since they are to be regarded as illustrative rather than restrictive. Variations and changes may be made by those skilled in the art without departing from the spirit of the invention.

REFERENCES

1. Osterud, B., and Rapaport, S. I. (1977) Proc. Natl. Acad. Sci. 74, 5260–5264
2. Davie, E. W., Fujikawa, K., and Kisiel, W. (1991) Biochemistry 30, 10363–10370
3. Mann, K. G., Krishnaswamy S., Lawson J. H. (1992) Hemostasis. Seminars in Hematolgy 29, 213–227
4. Gailani, D., and Broze, G. J. Jr (1991) Science 253, 909–912
5. Rapaport S. I. (1991) Thromb. Haemost. 66, 6–15
6. Sandset, P. M., Warner-Cramer, B. J., Rao, L. V. M., Maki, S. L., and Rapaport, S. I. (1991) Proc. Natl. Acad. Sci. 88, 708–712
7. Warner-Cramer, B. J., and Rapaport, S. I. (1993) Arterioscl. Thomb. 13, 1551–1557
8. Huang, Z. F., Wun, T. C., and Broze, G. J. (1993) J. Biol. Chem. 268, 26950–26955
9. Gemmel, C. H., Broze, G. J., Turitto, V. T., and Nemerson, Y. (1990) Blood 76, 2267–2271
10. van 't Veer, C., Hackeng, T. M., Delahaye, C., Sixma, J. J., and Bouma, B. N. (1994) Blood 84, 1132–1142
11. Blajchman, M. N., Austin, R. C., Fernandez-Rachubinski, F., Sheffield W. P. (1992) Blood 80, 2159–2171
12. Esmon, C. T. (1993) Thromb. Haemost 70, 29–35
13. Ohlin , A. K. and Marlar, R. A. (1995) Blood 85, 330–336
14. Griffin, J. H., Evatt, B., Zimmerman, T. S., Kleiss, A. J., and Wideman, C. (1981) J. Clin. Invest. 68, 1370–1373
15. Suzuki, K., Stenflo, J., Dahlback, B., and Teodorsson, B. (1983) J. Biol. Chem. 258, 1914–1920
16. Solymoss, S., Tucker, M. M., and Tracy, P. B. (1988) J. Biol. Chem. 263, 14884–14890
17. Vehar, G. A., and Davie, E. W. (1980) Biochemistry 19, 401–410
18. Marlar, R. W., Kleiss, A. J., and Griffin, J. H. (1982) Blood 59, 1067–1072
19. Fulcher, C. A., Gardiner, J. E., Griffin, J. H., and Zimmerman, T. S. (1984) Blood 63, 486–489
20. Eaton, D., Rodriguez, H., and Vehar, G. A. (1986) Biochemistry 25, 505–512
21. Koedam, J. A., Meijers, J. C. M., Sixma, J. J., and Bouma, B. N. (1988) J. Clin. Invest. 82, 1236–1243
22. Pitman, D. D., and Kaufman, R. J. (1988) Proc. NatL. Acad. Sci. USA 85, 2429–2433
23. Fay, P. J., Smudzin, T. M., and Walker, F. J. (1991) J. Biol. Chem. 266, 20139–20145
24. Dahlback, B., Carlsson, M., and Svensson, P. (1993) Proc. Natl. Acad Sci. USA 90, 1004–1008
25. Bertina, R. M., Koeleman, B. P. C., Koster, T., Rosendaal, F. R., Dirven, R. J., de Ronde, H., van der Velden, P. A., and Reitsma, P. H. (1994) Nature 369, 64–67
26. Kalafatis, M., Bertina, R.M., Rand, M. D., and Mann, K. G., (1995) J. Biol. Chem. 270, 4053–4057
27. Kalafatis, M., Rand, M. D., and Mann, K. G., (1994) J. Biol. Chem. 269, 31869–31880
28. Nesheim M E, Canfield W M, Kisiel W, Mann K G (1982) J. Biol. Chem. 257, 1443–1447
29. Krishnaswamy, S., Williams, E. D., and Mann, K. G. (1986) J. Biol. Chem. 261, 9684–9693
30. Dahlback, B. (1991) Throm. Haemostas. 66, 49–61
31. Solymoss, S., Tucker, M. M., and Tracy, P. B. (1988) J. Biol. Chem. 263, 14884–14890
32. Heeb, M. J,, Mesters, R. M., Tans, G., Rosing, J., and Griffin, J. H. (1993) J. Biol.Chem. 268:2872–2877
33. Hackeng, T. M., van 't Veer, C., Meijers, J. C. M., and Bouma, B. N. (1994) J. Biol. Chem. 269:21051
34. van 't Veer, C., Hackeng, T. M., Biesbroeck, D., Sixma, J. J., and Bouma, B. N (1995) Blood 85, 1815–1821
35. Comp, P.C., Nixon, R. R., Cooper M. R., and Esmon, C. T. (1984) J. Clin. Invest. 74, 2082–2088
36. Schwarz, H. P., Fischer, M., Hopmeier. P., Batard, M. A., and Griffin, J. H. (1984) Blood 64, 1297–1300
37. Rosing, J., Hoekema, L., Nicoleas, G. A. F., Thomassen M.C.L.G.D., Hemker H.C., Varadi, K., Schwartz H. P., and Tans, G. (1995) J.Biol. Chem. 270, 27852–27858
38. Lawson, J. H., Kalafatis, M., Stram, S., and Mann, K. G. (1994) J. Biol. Chem. 269, 23357–23366
39. Jones, K. C., and Mann, K. G. (1994) J. Biol. Chem. 269, 23367–23373
40. van 't Veer, C., and Mann, K. G. (1995) Blood 86 suppl 1, 448a, abstract 1777
41. van 't Veer, C., Kalafatis, M., and Mann, K. G. (1995) Blood 86 suppl 1, 285a, abstract 1128
42. Warshawsky, I., Bu, G., Mast, A., Saffitz, J. E., Broze, G. J., and Schwartz, A. L. Z. (1995) J. Clin. Invest. 95,1773–1781
43. Sandset, P. M., Abilgaard, U., and Larsen, M. L. (1988) Thromb. Res. 50, 803–813
44. Lindahl, A. K., Jakobsen, P. B., Sandset, P. M., and Abilgaard, U. (1991) Blood. Coag. Fibrin. 2, 713–721
45. Bregengaard, C., Nordvang, O., Ostergaad, P., Petersen, J. G. L., Meyn, G., Dinnes, V., Svendsen, O., and Hedner, U. (1993) Thromb. Haemostasis 70, 454–457
46. Bajaj, S. P., Rapaport, S. I., and Prodanos, C. (1981) Prep. Biochem. 11, 397–41219)
47. Nesheim, M. E., Katzmann, J. A., Tracy, P. B., and Mann, K. G. (1981) Methods Enzymol. 80, 249–274
48. Laemmli, U. K. (1970) Nature 227, 680–685
49. Towbin, H., Staehelin, T., and Gordon, J. (1979) Proc. And. Acad. Sci. U.S.A. 76, 4350–4354
50. Kalafatis, M., Lu, D., Bertina, R. M., Long, G. L., and Mann, K. G. (1995) Arteriosc. Thromb. Vasc. Biol. 12, 2181–2187
51. Mann, K. G., Kri masny, S., and Lawson, J. H. (1992) Seminars in Hemat. 3, 213–226
51. Vehar, G. A., and Davie, E. W. (1980) Biochemistry 19, 401–410
53. Lollar, P., Knutson, G. J., and Fass, D. N. (1985) Biochemistry 24, 8056–8064
54. Fay, P. J., Smudzin, T. M., and Walker, F. J. (1991) J.Biol. Chem. 266, 20139–20145
55. Lamphear, B. J., and Fay, P. J. (1992) Blood 80, 3120–3126
56. O'Brien, D. P., Johnson, D., Byfield, P., and Tuddenham, E. G. D. (1992) Biochemistry 31, 2805–2812
57. Lollar, P., and Parker, C. G. (1990) J. Biol. Chem. 265, 1688–1692
58. Fay, P. J., and Smudzin, T. M. (1992) J. Biol. Chem. 267, 1346–13250
59. Lollar, P., Parker, E. T. and Fay, P. J. (1992) J. Biol. Chem. 267, 23652–23657
60. Nicoleas, G. A. F., Tans, G., Thomassen M. C. L. G. D., Hemker H. C., Pabinger, I., Varadi, K., and Rosing, J. (1995) J. BioL. Chem. 270, 21158–2166
61. Suzuki, K., Dahlback, B., and Stenflo, J. (1981) J. Biol. Chem. 257, 6556–6564
62. Keller, F. G., Ortel, T. L., Quinn-Allen, M. A., and Kane, W. H. (1995) Biochemistry 34, 4118–4124

What is claimed is:

1. A method of identifying patients having an elevated risk for thrombosis, the method comprising the steps of:

measuring plasma tissue factor pathway inhibitor (TFPI) level of a patient;

determining if the patient carries a Factor $V^{LEIDEN}$ allele in his or her genome;

identifying a patient as being at elevated risk for thrombosis if the patient has a TFPI level lower than 89 mg/ml and a Factor $V^{LEIDEN}$ allele in his or her genome.

2. A method of identifying patients having an elevated risk for thrombosis, the method comprising the steps of:

measuring plasma tissue factor pathway inhibitor (TFPI) level of a patient;

determining if the patient carries a Factor $V^{LEIDEN}$ allele in his or her genome;

identifying a patient as being at elevated risk for thrombosis if the patient has a TFPI level lower than 53 mg/ml and a Factor $V^{LEIDEN}$ allele in his or her genome.

3. A method of identifying patients having an elevated risk for thrombosis, the method comprising the steps of:

measuring plasma tissue factor pathway inhibitor (TFPI) level of a patient;

determining if the patient carries a Factor $V^{LEIDEN}$ allele in his or her genome;

identifying a patient as being at elevated risk for thrombosis if the patient has a TFPI level lower than 72 mg/ml and a Factor $V^{LEIDEN}$ allele in his or her genome.

* * * * *

UNITED STATES PATENT AND TRADEMARK OFFICE
CERTIFICATE OF CORRECTION

PATENT NO. : 6,248,548 B1
DATED : June 19, 2001
INVENTOR(S) : Cornelis Van't Veer et al.

It is certified that error appears in the above-identified patent and that said Letters Patent is hereby corrected as shown below:

Title page,
Item [56] References Cited, OTHER PUBLICATIONS,
-- Katzung, Pasic-Clinical Pharmacology, Appleton-Lanage pp. 464-467 -- has been inserted,
Line 8, "van's" has been replaced with -- van't --.

Signed and Sealed this

Fourteenth Day of May, 2002

*Attest:*

JAMES E. ROGAN
*Attesting Officer*   *Director of the United States Patent and Trademark Office*

UNITED STATES PATENT AND TRADEMARK OFFICE
CERTIFICATE OF CORRECTION

| | |
|---|---|
| PATENT NO. | : 6,248,548 B1 |
| APPLICATION NO. | : 09/431103 |
| DATED | : June 19, 2001 |
| INVENTOR(S) | : Cornelis Van't Veer et al. |

Page 1 of 1

It is certified that error appears in the above-identified patent and that said Letters Patent is hereby corrected as shown below:

In Column 1 of the Specification, Line 3:
    Please insert the following sentence: --This invention was made using U.S. government NIH grant award No. HL046703. Therefore the U.S. government retains certain rights to the invention.--

Signed and Sealed this

Seventh Day of November, 2006

JON W. DUDAS
*Director of the United States Patent and Trademark Office*